United States Patent [19]

Huelsman

[11] 4,121,250
[45] Oct. 17, 1978

[54] FLICKER FREE SCAN CONVERSION SYSTEM

[75] Inventor: Kenneth A. Huelsman, Carlsbad, Calif.

[73] Assignee: Hughes Aircraft Company, Culver City, Calif.

[21] Appl. No.: 708,677

[22] Filed: Jul. 26, 1976

[51] Int. Cl.² .............................................. H04N 7/18
[52] U.S. Cl. .................................... 358/140; 358/112; 340/1 R; 343/5 SC
[58] Field of Search ............. 358/140, 112; 343/5 SC; 340/1 R

[56] References Cited

U.S. PATENT DOCUMENTS

| 3,218,637 | 11/1965 | Balding | 340/3 C |
|---|---|---|---|
| 3,810,174 | 5/1974 | Heard | 358/140 |
| 3,864,660 | 2/1975 | Ranalli et al. | 340/1 R |
| 3,925,606 | 12/1975 | Wood et al. | 358/140 |

Primary Examiner—Robert L. Griffin
Assistant Examiner—Edward L. Coles
Attorney, Agent, or Firm—Martin E. Gerry; William H. Mac Allister

[57] ABSTRACT

A scan conversion system having a synchronization generator that provides typical TV-style timing signals. A multivibrator connected to the generator has a two-state logic output of equal time duration to the timing signals of the generator. A binary logic circuit is activated by the multivibrator to trigger the scan converter wherein alternate read-write pulses are provided by the two-state logic of the multivibrator so as to eliminate picture flicker exhibited by the conventional system on the TV display.

24 Claims, 10 Drawing Figures

FLICKER FREE SCAN CONVERSION SYSTEM

BACKGROUND OF THE INVENTION

This invention is in the field of scan converters having TV-type displays, and more particularly in a scan converter system that provides scanned information substantially devoid of flicker.

The prior art systems, typically represented by U.S. Pat. No. 3,864,660 provides a group of consecutively scanned lines are read out followed by a blank space substantially of equal time duration as the read out consecutively scanned lines. Therefore, the first field will comprise say five solid lines and five missing lines in alternate fashion. The five missing lines will read into the blanked area from the second field. Therefore, in prior art systems, groups of visual information are displayed during one time duration repeated at a 30 cycle rate, and such 30 cycle repetition rate is well within the objectionable flicker range.

Another objective is to avoid in prior art systems the change from the read mode to the write mode of an entire large portion of the picture at one time (consisting of 5 to 7 lines at a time), and by so doing the TV screen at that time is blanked out. Such prior art functions and prior art objectives are disclosed in U.S. Pat. No. 3,864,660 wherein the patent specification shows an increase in flicker due to the described functions.

SUMMARY OF THE INVENTION

To achieve the objectives, the following distinguishing differences are present in the instant inventive system and absent in the prior art systems.

In the inventive system the video will appear on every other line of scanned lines. The video is interlaced as between even and odd fields, generally essentially the same as in standard TV system. However, in the inventive system the number of scanned lines will be one-half of the conventional TV system. Hence, every other line will be from every other field.

In the instant invention, however, we alternately write and read in every other scanned line thereby accomplishing two end results. The picture scanned is laid out in segments, thus allowing the TV monitor to receive information on every other scan line. This function gives information to the TV display at as high a rate as possible since we are permitting the system to read on every other scan line, resulting in interleaved scan lines and a picture without visible flicker.

Accordingly, scan conversion system having a scan converter and embodies first means for providing TV-type timing signals. Second means, electrically connected to the first means, provide two-state binary logic output signals therefrom of substantially equal time duration. Third means, connected to the second means, provide binary logic information to the scan converter.

An electronic counter is electrically connected to the output of the first means. Fourth means is electrically connected to the output of the counter, which activate the third and first means.

A transducer is electrically connected to the fourth means, where the output of the transducer is electrically connected to the input of the scan converter. An electronic visual display is electrically connected to the output of the scan converter, wherein the electronic visual display is of the cathode ray category or liquid crystal type.

The scan conversion system utilizes two fields per frame of visual information, substantially devoid of flicker. The system basically performs the following functions.

It senses intelligence information signals, the sensed signals comprising an odd multiple of TV line periods. It writes the sensed intelligence in segmentary format having a plurality of first set of segments which are one TV line in duration. It also writes the sensed intelligence in segmentary format having a plurality of a second set of segments which are one TV line in duration, and it interleaves the second set of segments with the first set of segments.

Further, the system electronically switches a synchronizing generator thereby providing an odd number of scan lines per field and an even number of scan lines per frame. The system then superimposes the switched scanned lines from the first field on to the scanned lines of the second field.

The system is capable of reading alternate lines of the first field and blanking out the lines between the alternate lines of the first field, and reading alternate lines of the second field and blanking out the lines between the alternate lines of the second field, and then interleaving the read lines of the first field with the read lines of the second field.

It is pointed out that steps of writing are effected during periods of said blanking, and that the writing is stored for a predetermined time period in the scan converter.

In summary, this system differs materially from other systems in that it makes possible the writing of interleaved segments of sensed intelligence in each of two reception periods, thereby resulting in complete information. By virtue of writing the information in segmentary form alternate read scan lines periods are allowed, which results in virtual elimination of flicker. Additionally, the system enables the occurrence of even number of scanned lines per frame, resulting in evenly interlaced read raster scanned TV-type lines, thereby eliminating paired scanned lines (because of the use of two fields) which would otherwise occur if alternate lines were read from a conventional odd-numbered TV line system, such as a 525 line system.

BRIEF DESCRIPTION OF THE DRAWINGS

FIGS. 4a-4c represent segments of two fields of view shown separately in FIGS. 4a and 4b, and shown in composite form, in FIG. 4c, when such two fields are interleaved.

DETAILED DESCRIPTION

Figure 1:
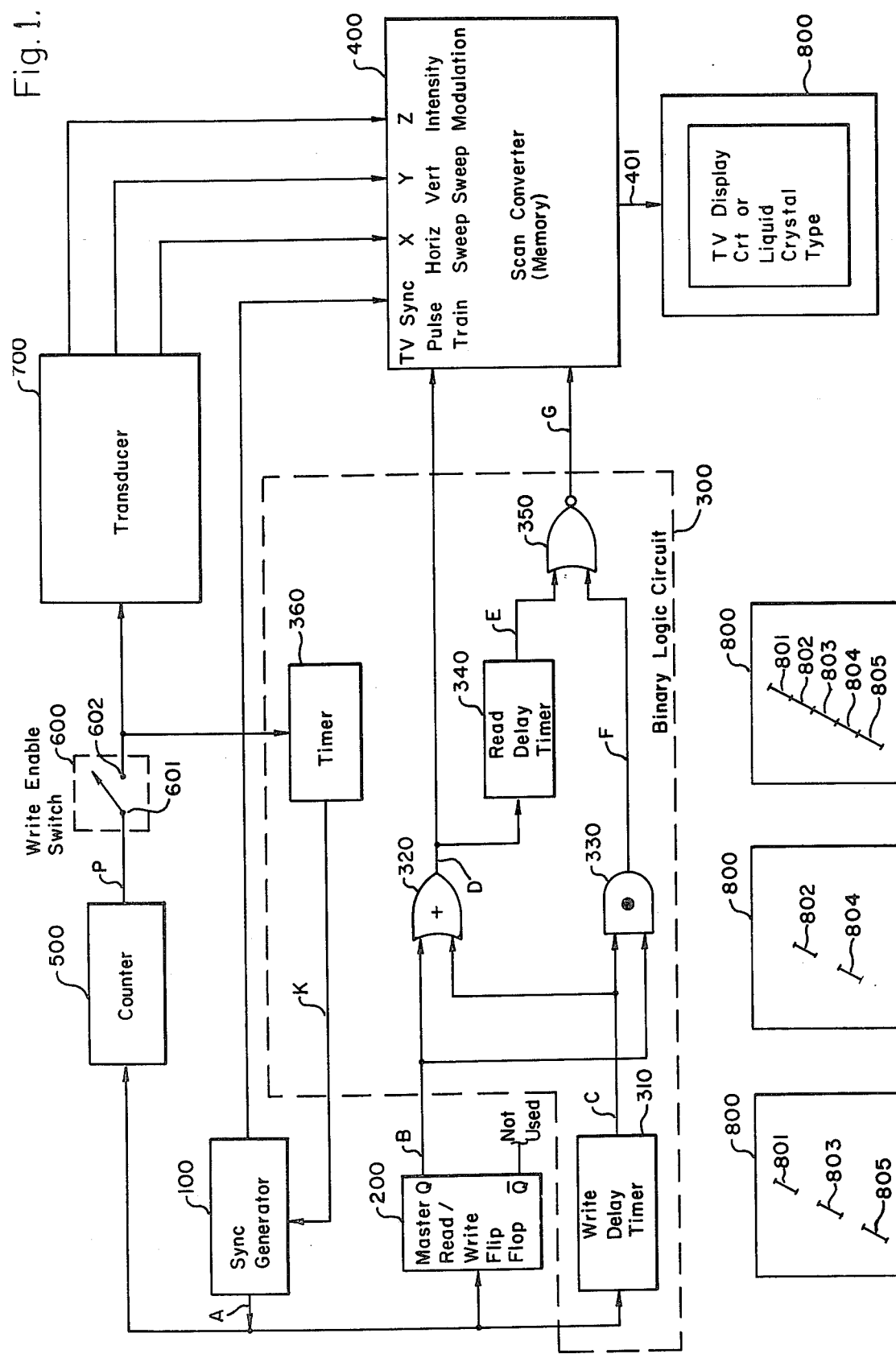
FIG. 1 is a schematic of the system embodying the invention.
Figure 2:
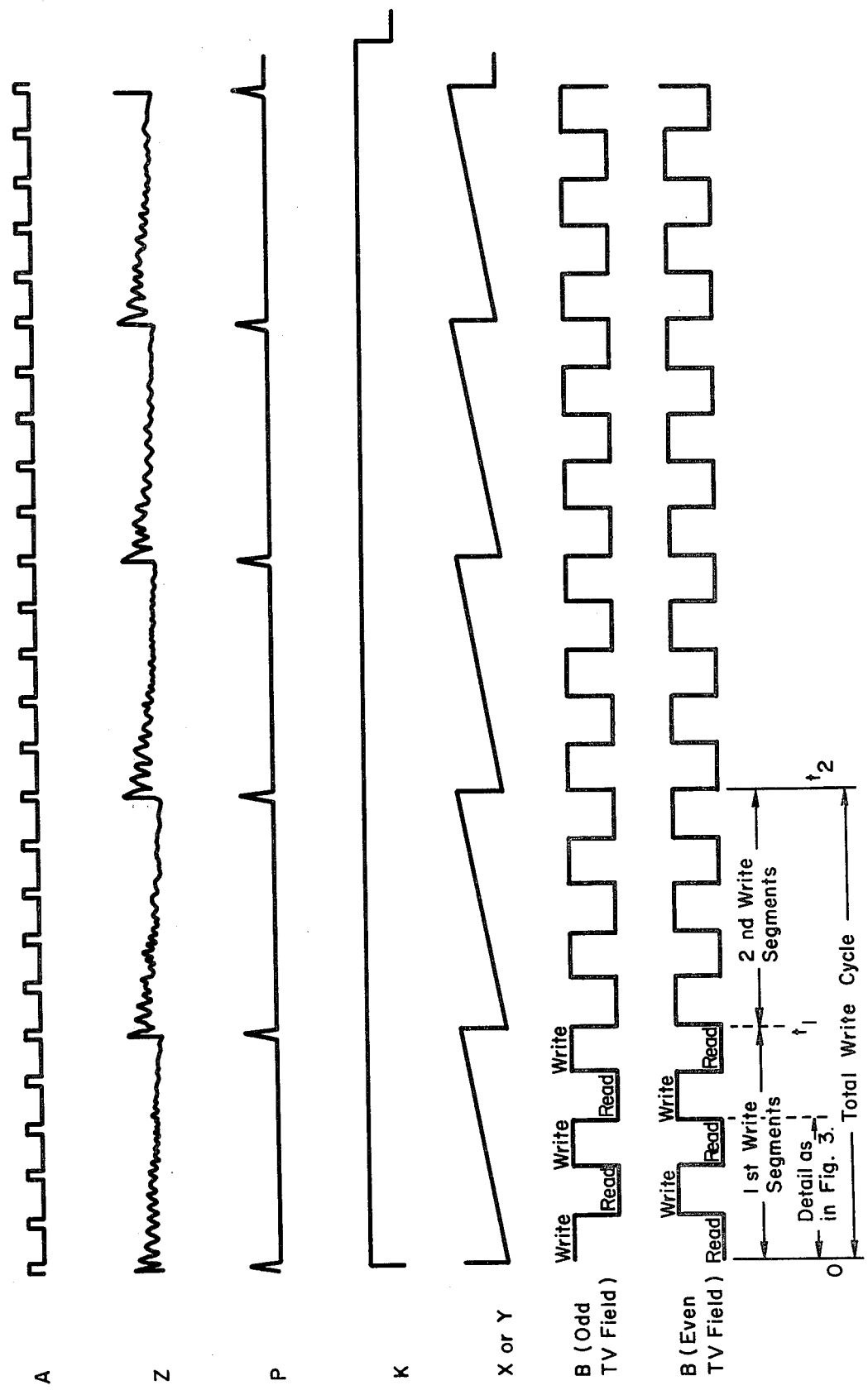
FIG. 2 is a group of timing waveforms of the system correlated to different portions of the system.
Figure 3:
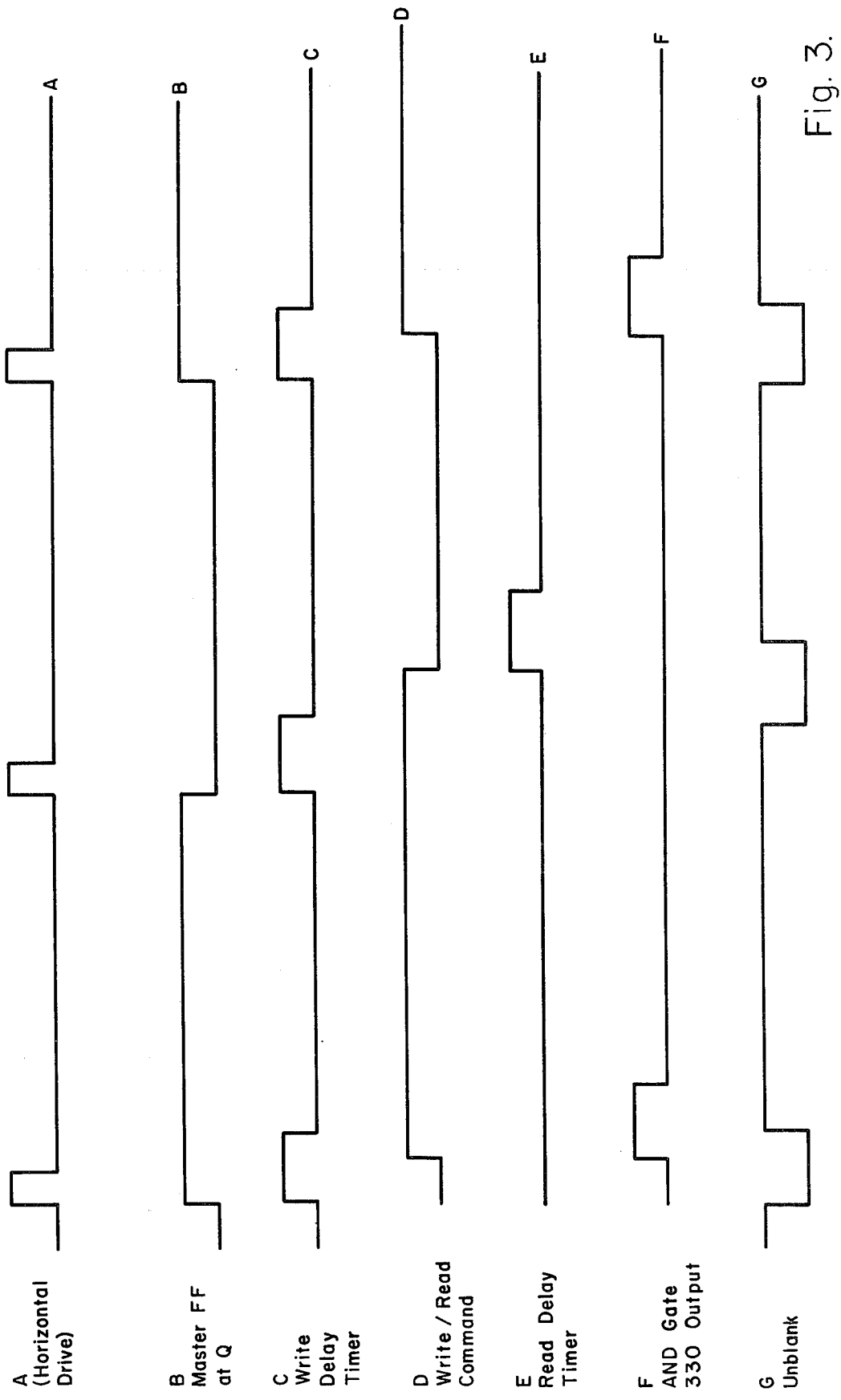
FIG. 3 is a group of timing waveforms showing an expanded portion of some of the waveforms in FIG. 2.

Referring to FIGS. 1, 2 and 3, a scan conversion system is displayed showing the combination of a synchronization generator 100 providing a TV-type timing signal. A bilateral switch 200 such as a conventional flip-flop circuit utilizes only one output, namely, the Q-type output, and is electrically connected to the output of generator 100. Such bilateral switch has two output states as part of the Q output. Both states are of equal time duration wherein each of the states has a time duration that is equal to the timing signals provided by generator 100. The $\bar{Q}$ output is not used.

A binary logic circuit is provided at 300, the input of which is electrically connected to switch 200.

The scan conversion system includes a scan converter 400 having a memory therein which is electrically connected to the output of logic circuit 300.

An electronic counter 500 is electrically connected to the output of the sync generator 100.

Sync generator 100 provides an output at A consisting of a series of rectangular pulses spaced at regular intervals. It is pointed out that the Q output of flip-flop 200 has the waveform as is shown at B.

It is also pointed out that the outputs of logic circuit 300 is shown in terms of waveforms D and G as an input to scan converter 400. Also the output of sync generator 100 provides a TV-type sync pulse per frame as an input to scan converter 400.

Counter 500 provides an input to movable contactor 601 of write enable switch 600. The waveform designated at P is therefore an output of counter 500.

When switch 600 is closed, causing contactors 601 and 602 to cooperate, the P waveform will be present as an input to transducer 700 and also as an input to a timer designated as 360 which is part of binary logic system 300, to be hereinbelow discussed. Timer 360 also provides an output which is inputted to sync generator 100. The output of the timer is shown by waveform as type K. Therefore, when switch 600 is closed the system writes the information received by transducer 600, and when switch 600 is open the system only reads such incoming information.

Transducer 700 has outputs at X, Y and Z, which are inputs to scan converter 400; X, Y and Z signals are shown graphically in the drawings. Details of this transducer are shown in U.S. Pat. No. 3,864,660 as components 10, 11, 13, 14 and 25 therein. Therefore, no further illustration of transducer 700 is needed. It is, however, pointed out that transducer 700 as shown in the referenced patent is not a limitation as to the type of transducers that may be used in this inventive system. Typical transducers providing such outputs as described, and triggered by inputs as described may be utilized. Such transducers are used in radar and infrared systems and the like.

Scan converter 400 provides a composite TV video signal at 401, which is provided as an input to TV display 800. Display 800 may be of a cathode ray tube type, or the liquid crystal type.

Accordingly, when switch 600 is closed, counter 500 will provide the P waveform as inputs to both transducer 700 and timer 360.

It is also obvious that since sync generator 100 puts out waveform type A, that such waveform will be provided as an input to counter 500, to the master read/write flip-flop 200 and as an input to the write delay timer 310.

With special reference to the binary logic circuit 300, it may be seen that master flip-flop output from its Q terminal will provide a B-type waveform as an input to non-exclusive OR gate 320. The B waveform will also be provided as an input to AND gate 330. Similarly, the output of write delay timer 310 will provide its output waveform type C as inputs to both gates 320 and 330.

When OR gate 320 will both have positive-going pulses, then during the time duration of such positive-going pulses as inputs to the gate, a binary ONE output will obtained as waveform type D to serve as input to the scan converter 100 and to the read delay timer 340. It should be noted that the read delay timer will provide a delay time pulse output as denoted at E with respect to the READ commands received thereby. Such waveform as at E will provide an input to NOR gate 350. The output of AND gate 330 will provide an F-type waveform only when both inputs to such gate, namely, waveforms B and C, will positive-going pulses, and therefore, are logic ONE signals. The output of AND gate 330 is shown as a logical ONE pulse output of such gate at F as an input to NOR gate 350. Consequently, when inputs E and F are present, to trigger NOR gate 350, an unblanking signal will be provided as shown by waveform G as an input to the memory within scan converter 400. The purpose of the blanking and unblanking will be subsequently discussed.

Consequently, the waveform K output of timer 360, which is part of the binary logic circuit 300, will provide an input to sync generator 100 when switch 600 is closed, so as to change the number of scanning lines of said generator from an odd to an even number of lines when contactors 601 and 602 cooperate. Remembering that in conventional TV scan system, two fields per frame are utilized, such as used herein, and referring again to the B waveforms, it may be seen that comparing the two waveforms, wherein one shows the TV odd field and the other shows the TV even field, during a WRITE mode for example, as a TV odd field, indicates a logical ONE condition; when in the READ mode of the TV even field situation a logical ZERO is present. The READ and WRITE modes represented by each of the fields, alternate with respect to each other during the switching action of the master Read/Write flip-flop output of Q as shown in FIG. 1.

Referring also to FIGS. 4a, 4b, and 4c, and to the intensity modulation pattern at Z as output of transducer 700, which transducer senses such intelligence information signals applied as an input thereto, in similar manner as shown in U.S. Pat. No. 3,864,660, or like type devices. Such sensed information signals comprise an odd multiple of TV line periods as may be seen by examining the TV odd field pattern as shown in waveform at B. During such sensed period, exemplified by the time span indicated in FIG. 1 as $0-t_1$, alternate segments of the sensed information are written, as shown by segments 801, 803, and 805 which have spacing therebetween equal in length to each of the stated segments which, in this example are displayed on the screen of the cathode ray TV or liquid crystal type display 800. During the second reception period of information within the time span $t_1-t_2$, a second group of segments are recorded as exemplified by individualized segments 802 and 804, which segments 802 and 804 are interleaved respectively between 801–803 and 803–805. The end result is shown as a continuous pattern comprising segments 801, 802, 803, 804, and 805.

Figure 5A:
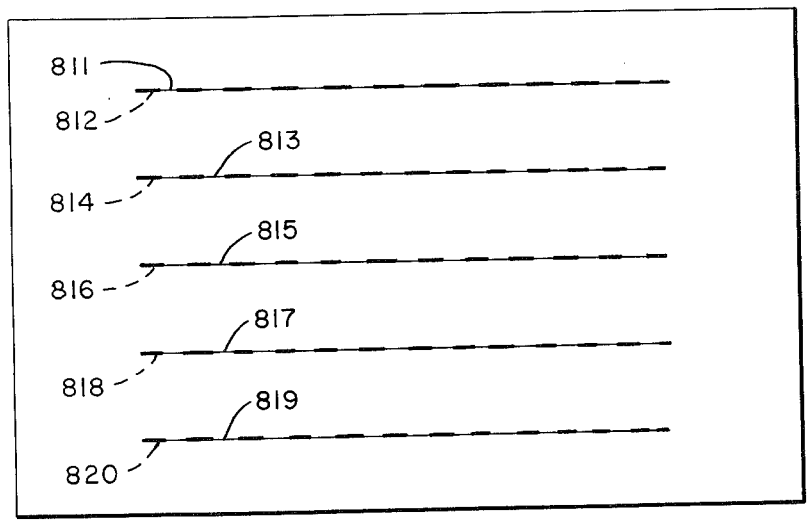
FIG. 5a shows a group of scanning lines from two fields overlayed upon each other.
Figure 5B:
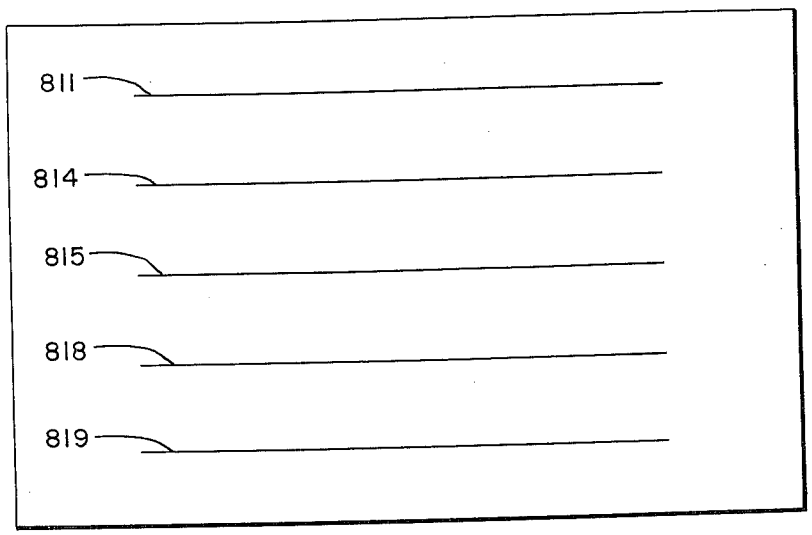
FIG. 5b shows alternate field scanned lines where lines therebetween as in FIG. 5a are blanked.

With additional reference to FIGS. 5a and 5b, representing TV scanned line readout, and remembering that when switch 600 is closed, timer 360 is thereby initiated, which in turn provides an input as at K to sync generator 100, switching it to an even number of lines per frame from the normal odd number of lines present in a conventional TV system, thereby resulting in spatial coincidence of field number-one lines, 811, 813, 815, 817, and 819, superimposed respectively over field number-two lines, 812, 814, 816, 818, and 820.

By virtue of switching flip-flop 200 alternately from one state to another at its Q terminal, and action of gate 320, the requisite READ-WRITE command is provided at 321, so as to enable alternate lines of the first field 811, 815, and 819 to be read while lines 813 and 817 are blanked out. During such blanking interval is the time when the prior referred-to written segments 801–805 occur. Likewise, lines of the second field 814 and 818 are read while lines 812, 816, and 820 are blanked out, thereby resulting in an exemplary 5 line raster, used for illustration of the principles of this invention and illustrated in FIG. 5b. As stated above, the functions of writing are effective during periods of the blanking action.

It should be appreciated that a memory, to store the incoming information from the system, as part of the scan converter is necessary in certain applications. For example, the particular system illustrated is applicable to obtain a cross-section of the vital organs within a human body. In order to be able to store sufficient information so as to plot the complete and actual cross-section thereof, scanning of the particular portion of the human body by a suitable transducer, for example, an ultrasound transducer, as connected to and part of transducer 700 discussed in exemplary fashion in U.S. Pat. No. 3,864,6760, a predetermined number of scans will have to be made and the images thereof stored within the scan converter. It is, of course, appreciated that plotting and displaying a scanned simple pattern comprising of segments 801–805 as heretofore described on the face of the CRT display tube would require very little in terms of memory and storage time within such scan converter. However, scanning an organ such as a heart, or a lung, or liver, or the like, would require many more scans than the illustrated in FIGS. 4a–4c. Therefore, there is a need for a memory which may be magnetic tape or similar type memory in scan converter 400 so as to play back the intensity modulated output of the pattern stored and display it on the face of the CRT or the liquid crystal type TV display 800.

This system differs materially from other systems in that it makes possible the writing of interleaved segments of sensed intelligence in each of two reception periods, thereby resulting in complete information. By virtue of writing the information in segmentary form alternate READ scan lines periods are allowed, which results in virtual elimination of flicker. Additionally, the system enables the occurrence of even number of scanned lines per frame, resulting in evenly interlaced read raster scanned TV type lines, thereby eliminating paired scanned lines (because of the use of two fields) which would otherwise occur if alternate lines were read from a conventional odd-numbered TV line system, such as a 525 line system.

Figure 6:
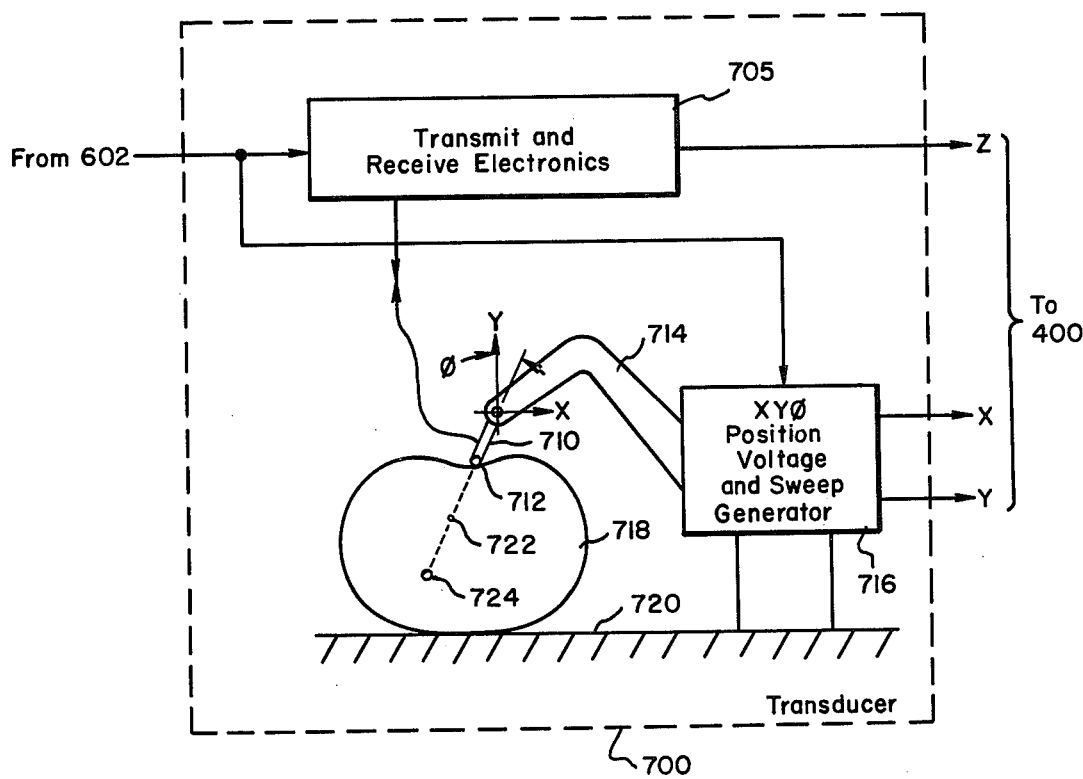
FIG. 6 is a schematic of details of the transducer subsystem shown in FIG. 1.

Referring to FIG. 6, details of transducer 700, which are also shown in U.S. Pat. No. 3,864,660 are now described.

In operation, an electrical pulse from the transmit receive electronics 705 is connected to the transducer 710 where it is converted to an ultrasonic pulse radiated from end 712 of the transducer. The transducer is carried on an arm 714 of the position voltage generator 716. The transducer is moved over body 718 which may rest on a table or other support 720, with the operator moving the transducer in the $x$ and $y$ directions and also pivoting the transducer with respect to arm 714, with the pivoting angle $\phi$.

Echos are generated by the surface of the body 718 and by discontinuities within the body, as indicated by the dots 722 . . . 724. The echos are picked up by the transducer, converted to electrical signals, and connected to the receiver portion of 705 for subsequent transmission to the scan converter of the display unit. The echo pulse information is written or stored in the scan converter with the position being determined by the position voltages from generator 716, all in the conventional manner. During the read mode of operation, the stored image is read by a conventional TV sweep as modified and hereinabove described and displayed on a conventional TV monitor such as at 800. The echos from a single pulse are illustrated in body 718 and in the display at 800. However, in actual use, a large number of ultrasonic pulses from a large number of positions and angles are utilized to provide a complete picture of the body being analyzed.

Figure 7:
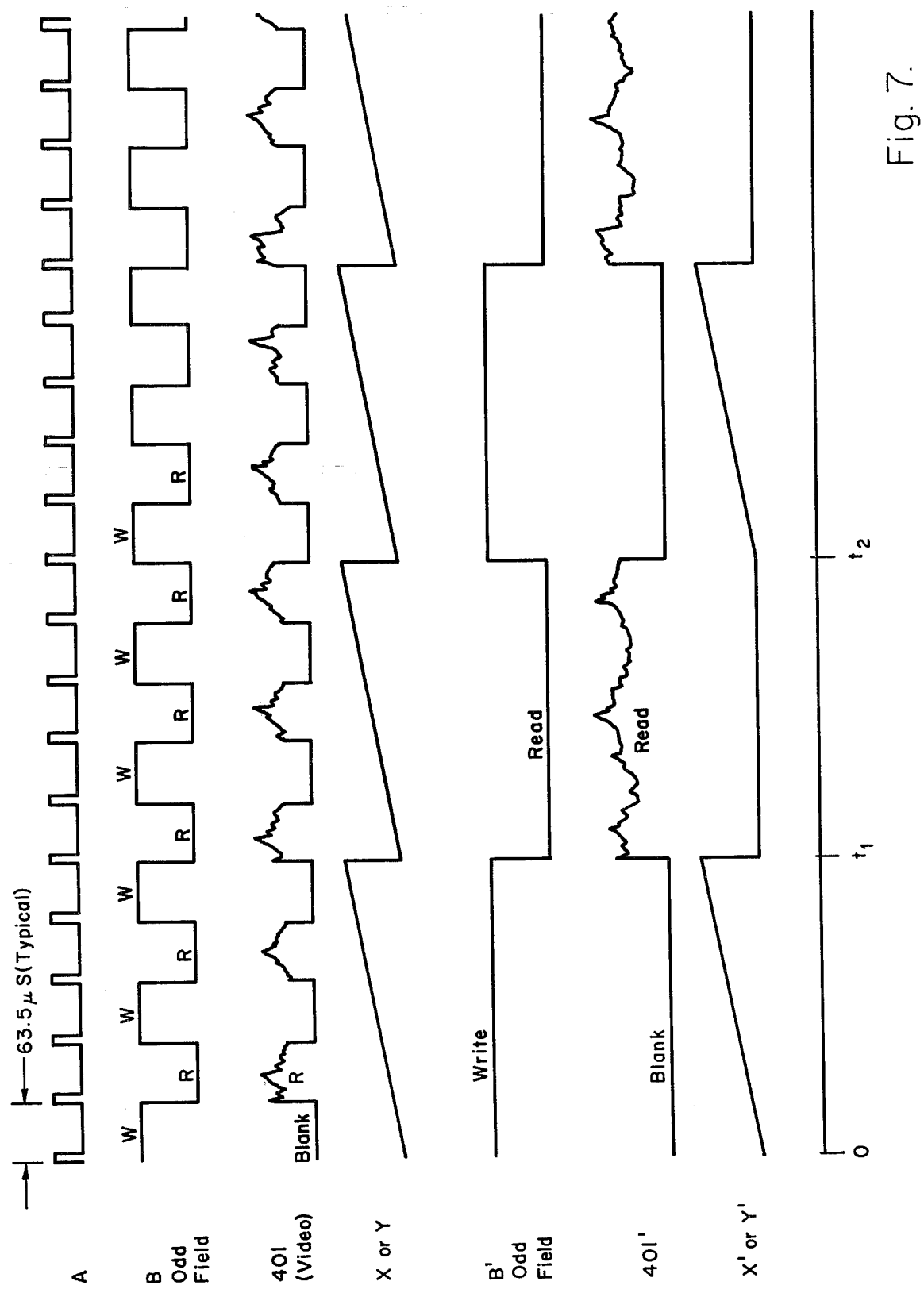
FIG. 7 comprises part of groups of waveforms shown in FIGS. 2 and 3, compared with waveforms produced by the prior art systems.

Referring to FIG. 7, a comparison between certain functions performed by the inventive system, shown by waveforms B, X or Y, and 401 video with the prior art analogous waveforms B′, X′ or Y′, and 401′ video gives an appreciation for distinguishing features. It should be noted that sync generator 100 output at A is the same in the prior art systems, have a pulse repetition period typically of 63.5 microseconds. A common time base $0-t_1$ and $t_1-t_2$ is used for ease of comparison of inventive and prior art systems.

In the inventive system, the video will appear on every other line of scanned lines. The video is interlaced as between even and odd fields, generally essentially the same as in standard TV systems. However, in the inventive system, the number of scanned lines will be one-half of the conventional TV system. Hence, every other line will be from every other field.

However, in the prior art systems such as exemplified by U.S. Pat. No. 3,864,660, a group of consecutively scanned lines are read out followed by a blank space substantially of equal time duration as the read out consecutively scanned lines. Therefore, the first field will comprise say five solid lines and five missing lines in alternate fashion. The five missing lines will be read into the blanked area from the second field. Therefore, in prior art systems, groups of visual information are displayed during one time duration repeated at a 30 cycle rate, and 30 cycle rate repetition is well within the objectionable flicker range.

In the instant invention, however, we alternately write and read on every other scanned line thereby accomplishing beneficial end results. The picture scanned is laid out in segments thus allowing the TV monitor to receive information on every other scan line. This function gives the information to the TV display at as high a rate as possible since we are permitting the system to read on every other scan line, resulting in an interleaved scan lines and a picture without visible flicker. Such functions are shown in FIGS. 2 and 7 by waveforms B, X or Y, and the video at 401.

The prior art system on the other hand changes from the read mode to write an entire large portion of the picture at one time (consisting of 5 to 7 lines at a time), and by so doing the TV screen at that time is blanked out as shown in FIG. 7 by B′, 401′ and X′ or Y′ waveforms. Such prior art functions and objectives are disclosed in U.S. Pat. No. 3,864,660 wherein the patent specification admits an increase in flicker due to the described functions.

What is claimed is:

1. In a scan conversion system, the combination comprising:
   a sychronization generator providing TV-type timing signals;
   a bilateral switch, electrically connected to the output of the generator, said bilateral switch having two states, both states being of equal time duration, wherein each of said states has a time duration equal to said timing signals;
   a binary logic circuit the input of which is electrically connected to said switch;
   a scan converter electrically connected to the output of the logic circuit;
   an electronic counter electrically connected to the output of the generator;
   a switch member electrically connected to the output of the counter; and
   a transducer electrically connected to the switch member, the output of the transducer being electrically connected to the input of the scan converter.

2. The invention as stated in claim 1, including an electronic visual display electrically connected to the output of the scan converter.

3. The invention as stated in claim 2, wherein the electronic visual display is of the cathode ray category.

4. The invention as stated in claim 2, wherein the electronic visual display is of the liquid crystal type.

5. In a scan conversion system, the combination comprising:
   a synchronization generator providing TV-type timing signals;
   a bilateral switch, electrically connected to the output of the generator, said bilateral switch having two states, both states being of equal time duration, wherein each of said states has a time duration equal to said timing signals;
   a binary logic circuit the input of which is electrically connected to said switch;
   a scan converter electrically connected to the output of the logic circuit;
   an electronic counter electrically connected to the output of the generator; and
   a switch member electrically connected to the output of the counter, the output of the switch member being electrically connected to the logic circuit.

6. The invention as stated in claim 5, wherein an output of the logic circuit is electrically connected to an input of the generator so as to change the number of scanning lines of said generator when said switch member is closed.

7. In a scan conversion system, the combination comprising:
   a synchronization generator providing TV-type timing signals;
   a bilateral switch, electrically connected to the output of the generator, said bilateral switch having two states, both states being of equal time duration, wherein each of said states has a time duration equal to said timing signals;
   a binary logic circuit the input of which is electrically connected to said switch the binary logic circuit including:
      a write-delay timer electrically connected to the output of the generator;
      a non-exclusive binary OR gate electrically connected to the output of the bilateral switch;
      a binary AND gate electrically connected to the outputs of the bilateral switch and the write-delay timer;
      a read-delay timer electrically connected to the output of the OR gate; and
      a binary NOR gate electrically connected to the outputs of the read-delay timer and the AND gate;
   a scan converter electrically connected to the output of the logic circuit;
   an electronic counter electrically connected to the output of the generator; and
   a switch member electrically connected to the output of the counter.

8. The invention as stated in claim 7, wherein the outputs of the NOR gate and the OR gate are both electrically connected to the input of the scan converter.

9. In a scan conversion system, the combination comprising:
   a synchronization generator providing TV-type timing signals;
   a bilateral switch, electrically connected to the output of the generator, said bilateral switch having two states, both states being of equal time duration, wherein each of said states has a time duration equal to said timing signals;
   a binary logic circuit the input of which is electrically connected to said switch;
   a scan converter electrically connected to the output of the logic circuit;
   an electronic counter electrically connected to the output of the logic circuit;
   a switch member electrically connected to the output of the counter; and
   a transducer electrically connected to the switch member said transducer having an X-sweep, Y-sweep and Z-axis outputs which are all electrically connected to the input of the scan converter.

10. In a scan conversion system, the combination comprising:
    first means for providing TV-type signals;
    second means, electrically connected to the first means, for providing two state binary logic output signals therefrom of substantial equal time duration;
    third means, connected to the second means, for providing binary logic information to the system;
    a scan converter connected to the third means;
    an electronic counter electrically connected to the output of the first means;
    fourth means electrically connected to the output of the counter, for activating the third and first means;
    a transducer electrically connected to the fourth means, the output of said transducer being electrically connected to the input of the scan converter.

11. The invention as stated in claim 10, including an electronic visual display electrically connected to the output of the scan converter.

12. The invention as stated in claim 11, wherein the electronic visual display is of the cathode ray category.

13. The invention as stated in claim 11, wherein the electronic visual display is of the liquid crystal type.

14. In a scan conversion system utilizing two fields per frame of visual information substantially devoid of flicker, the steps comprising in combination:

(a) sensing intelligence information signals, the sensed signals comprising an odd multiple of TV line periods;
(b) writing the sensed intelligence in segmentary format having a plurality of first set of segments which are one TV line in duration;
(c) writing the sensed intelligence in segmentary format having a plurality of a second set of segments which are one TV line in duration;
(d) interleaving the second set of segments with the first set of segments; and
(e) electronically switching a synchronizing generator thereby providing an odd number of scan lines per field and an even number of scan lines per frame.

15. The invention as stated in claim 14, including the further step of:
(f) superimposing the switched scanned lines from the first field on to the scanned lines of the second field, subsequent to step (e).

16. The invention as stated in claim 15, including the further steps:
(g) reading alternate lines of the first field and blanking out the lines between the alternate lines of said first field, subsequent to step (f);
(h) reading alternate lines of the second field and blanking out the lines between the alternate lines of said second field, subsequent to step (g); and
(i) interleaving the read lines of the first field with the read lines of the second field, subsequent to step (h).

17. The invention as stated in claim 16, wherein the steps of writing are affected during periods of said blanking.

18. The invention as stated in claim 17, wherein the writing is stored for a predetermined time period.

19. A flicker-free visual display system having a transducer feeding a scan converter memory and utilizing two fields per raster frame readout, comprising the combination:
first means for writing odd and even number of segmentary portions of lines in alternation for each repetition period of output from said transducer; and
second means comprising a TV type viewer and said scan converter memory feeding said viewer for inhibiting the display of alternate lines of each of the raster fields.

20. The invention as stated in claim 19, wherein said second means provides an odd number of TV lines per field and an even number of TV lines per raster frame.

21. The invention as stated in claim 19, wherein said first means includes:
a write enable switch providing electrical continuity therethrough during the write mode and feeding the transducer;
an electronic counter feeding the write enable switch;
a synchronization generator feeding the counter;
a read-write binary switch fed by the generator; and
a logic circuit fed by the binary switch, the synchronization generator and the write enable switch.

22. A flicker-free visual display system having a transducer feeding a scan converter memory utilizing two fields per raster frame readout, comprising the combination:
first means for writing an odd number of segmentary portions of lines for a first repetition period of output from the transducer, said first means also enabling the writing of an even number of segmentary portions of said lines for the next repetition period of output from said transducer in alternation with said first repetition period; and
second means comprising a TV type monitor and said scan converter memory feeding said monitor for reading alternate lines of each said two fields per said raster frame readout.

23. The invention as stated in claim 22, wherein said first and second means provide an odd number of TV lines per field and an even number of TV lines per raster frame.

24. The invention as stated in claim 22, wherein said first means includes:
a write enable switch providing electrical continuity therethrough during the write mode and feeding the transducer;
an electronic counter feeding the write enable switch;
a synchronization generator feeding the counter;
a read-write binary switch fed by the generator; and
a logic circuit fed by the binary switch, the synchronization generator and the write enable switch.

* * * * *